United States Patent [19]

Wymer

[11] 4,258,843
[45] Mar. 31, 1981

[54] VESSELOOP DISPENSING PACKAGE

[75] Inventor: Carl G. Wymer, St. Paul, Minn.

[73] Assignee: Med General, Inc., Minneapolis, Minn.

[21] Appl. No.: 80,492

[22] Filed: Oct. 1, 1979

[51] Int. Cl.³ ............................................. A61B 17/06
[52] U.S. Cl. ................................. 206/63.3; 206/49; 206/388; 242/85.1; 242/125.1
[58] Field of Search ............... 206/388, 49, 63.3; 40/309; 242/85.1, 125.1, 125.2, 125, 125.3, 222; 223/106

[56] References Cited

U.S. PATENT DOCUMENTS

| | | | |
|---|---|---|---|
| 1,914,836 | 6/1933 | Randall | 206/63.3 |
| 2,590,799 | 3/1952 | Solowey | 206/63.3 |
| 2,993,589 | 7/1961 | Zoller et al. | |
| 3,357,550 | 12/1967 | Holmes et al. | 206/63.3 |
| 3,490,192 | 1/1970 | Regan, Jr. | |
| 3,728,839 | 4/1973 | Glick | 206/63.3 |
| 3,779,375 | 12/1973 | Foster | |
| 3,951,261 | 4/1976 | Mandel et al. | |
| 4,069,912 | 1/1978 | Black et al. | |
| 4,161,075 | 7/1979 | Eubanks et al. | 206/388 |

*Primary Examiner*—Joseph Man-Fu Moy
*Attorney, Agent, or Firm*—Orrin M. Haugen; Thomas J. Nikolai

[57] ABSTRACT

A dispenser package for vessel occluding bands used in surgical procedures. A thin rectangular plastic card or sheet is provided with winding notches or grooves along opposed edges thereof, such that one or more bands or strands of elastic material may be wound on the card with the individual turns of the strand being spaced from one another. To keep the elastic band from unraveling from the card, slits are formed on the remaining opposed edges of the card and a tongue slit is formed centrally of the card such that one free end of the band can be retained in one of the edge slits and the other free end is retained in the tongue slit. An outer sleeve of transparent plastic film material is adapted to surround the card with the bands wound thereon to help ensure cleanliness of the bands, while allowing them to be dispensed from the card without removal of the card from the sleeve.

1 Claim, 3 Drawing Figures

VESSELOOP DISPENSING PACKAGE

BACKGROUND OF THE INVENTION

I. Field of the Invention:

This invention relates to an improved packaging arrangement for surgical materials and more specifically to a package which facilitates the handling and dispensing of elastic bands useful in occluding various body vessels during surgical procedures.

II. Discussion of the Prior Art:

Several years ago a product was made available to surgical personnel for facilitating the occlusion of blood vessels and other fluid transporting ducts in the body, this product taking the form of an elastic band having an oval cross-section and formed from a radiopaque siliconerubber material. These bands could be wrapped about the vessel to be occluded and secured in place by a suitable clamp. The product in question also is available in different colors, such that a predetermined color coding scheme can be utilized in readily identifying the type of vessel being occluded by that particular band.

In packaging such occluding bands for distribution and use within an operating room environment, it has been the practice in the past to merely include a plurality of bands in loose fashion within a folded paper or cardboard envelope. Once the envelope is opened, the individual bands fall loose and became entangled one with the other so that it has been somewhat cumbersome to rapidly select only a single band from the package for tying off a particular vessel. It is readily apparent that, in an operating room setting, loss of a very few seconds can result in serious consequences to the surgery patient.

The packaging scheme of the present invention is intended to overcome the foregoing prior art deficiency. That is, the packaging scheme described in detail herein allows one of a plurality of vessel occluding bands to be withdrawn from its sterile package without becoming tangled with similar bands remaining within this package.

SUMMARY OF THE INVENTION

In its simplest form, the vessel occluding band package of the present invention comprises an inner card member formed from a thin plastic sheet into a generally rectangular configuration having a pattern of rounded notches on first and second opposed edges thereof. In one version, the notches are along the width dimension of the card and in another version the rounded notches are aligned along the length dimension. The remaining side edges of the card or sheet have inwardly extending slits formed therein. Furthermore, the card includes a plurality of tongue-like tabs defined by three-sided cutouts which are located inwardly of the notched side edges and extend in opposite directions parallel thereto.

The card is designed to hold one or more lengths of extruded elastic bands of the type used to occlude blood vessels and the like during surgical procedures. One end of the extruded strand is inserted through the slit on one side edge of the card and it is wrapped between the opposed notches on the adjacent edges. The remaining free end of the extruded elastic band is then inserted into and held by one of the tongue-like tabs. In a similar fashion, a second length of extruded plastic may be wound upon the same card and have its ends releasably held in the aforementioned slits.

Completing the package is an outer sleeve which is formed from a suitable plastic film and is generally rectangular and slightly larger in length and width than the card member described above. The sleeve is open along two opposed edges and sealed or joined along opposed edges which are adjacent to the opened ones. Thus, the card with the extruded length of plastic may be inserted into the plastic film sleeve through one or the other of the open side edges.

The sleeve provides protection from contamination while permitting one or the other of the two elastic bands to be withdrawn from the package without the necessity of first removing this protective sleeve. Because of the simple construction involved, the overall cost of the package is relatively low. In addition, the outer protective sleeve provides a convenient surface on which alphanumeric or other graphic information may be displayed.

OBJECTS

It is accordingly a principle object of the present invention to provide a new and improved package for containing and dispensing elastic, vessel occluding bands for use in the course of surgical procedures.

Another object of the invention is to provide a low-cost, simple, dispenser package for surgical apparatus which is readily sterilized and shielded from contamination.

A still further object of the invention is to provide a package for holding and dispensing vessel occluding bands in a manner which permits the surgeon to withdraw, one-at-a-time, the bands for application to a body vessel without becoming tangled with additional bands which may be contained within the same package.

These and other objects and advantages of the invention will become apparent to those skilled in the art from the following detailed description of the preferred embodiment in which like numerals in the several views refer to corresponding parts.

DESCRIPTION OF THE PREFERRED EMBODIMENT

Figure 1:
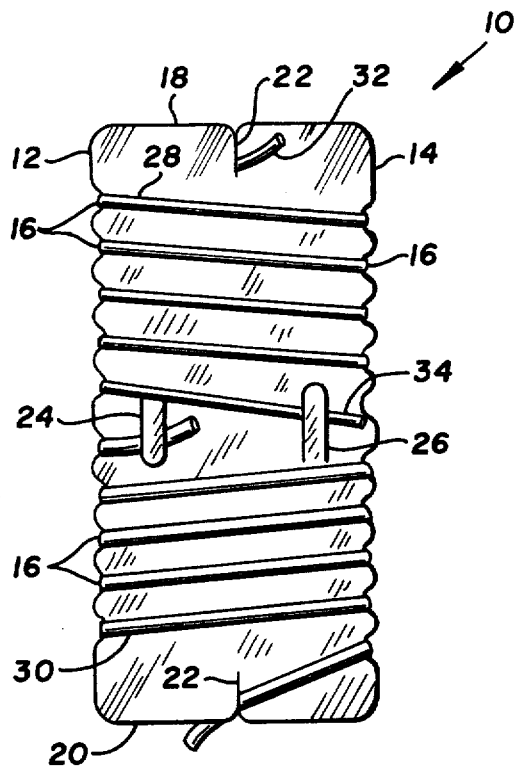
FIG. 1 is a plan view of one form of insert card having the elastic band material to be dispensed wound thereon.

Referring first to FIG. 1, there is indicated generally by numeral 10 the inner card portion of the composite packaging arrangement for the elastic vessel occluding bands. The card 10 comprises a generally rectangular sheet of a suitable plastic material such as a high density polyethylene which may, for example, be approximately 0.02 inches in thickness. Extending along the length dimension of the card 10 on opposed side edges 12 and 14 are a series of rounded notches as at 16. The notches are preferably arranged such that the crest on one side edge is aligned with the trough on its opposed side edge.

The remaining side edges 18 and 20 each include a slit as at 22 which extends inwardly from the edge for a predetermined distance. Offset inwardly from the notched longitudinal edges of the card 10 are first and second tongue-like tabs 24 and 26 which extend generally parallel to the edges 12 and 14 and are formed by slitting the card along three contiguous line segments as illustrated.

The manner in which the elastic band material is wrapped on the card 10 can also be readily observed from FIG. 1. In this arrangement, two separate bands 28 and 30 are wrapped on the card. A first end 32 of the band 28 passes through the slit 22 and is then wrapped about the card with individual turns extending between the notches 16 formed along the side edges 12 and 14, respectively. The remaining free end of the band 28 is identified by numeral 34 and this end is secured under the tongue tab 26 to preclude the band 28 from becoming unwound. In a similar fashion, the free ends of the band 30 are secured by the tab 24 and the slit 22 which is formed in the end edge 20 of the card.

Figure 2:
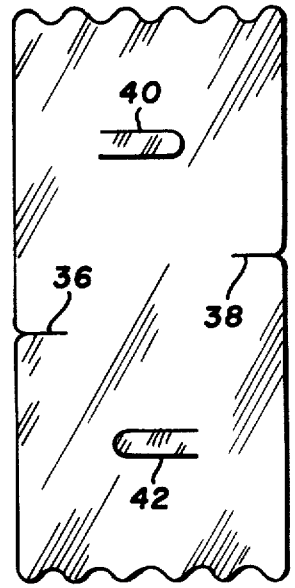
FIG. 2 is an alternative form of the insert card of FIG. 1, but without the elastic band material thereon.

FIG. 2 is intended to illustrate the construction of the inner card member when the rounded notches are formed in the edges defining the narrower width dimension rather than in the longer longitudinal edges. Again, the card of FIG. 2 is equipped with the slits 36 and 38 extending inwardly from the smooth (unnotched edges) and the oppositely facing tongue tabs 40 and 42 formed by slitting through the thickness dimension of the card member along three continuous line segments. Again, the card of FIG. 2 is designed to hold at least two elastic band members which are to be wrapped upon the card so that individual turns fall in the opposed notches on the transverse edges with the free ends of the bands being secured in slit 36 and tab 40 or slit 38 and tab 42.

Figure 3:
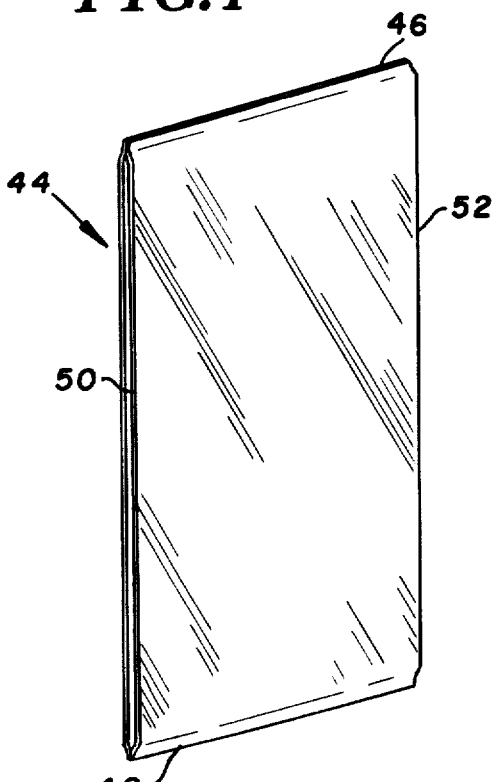
FIG. 3 is a plan view of the sleeve member adapted to surround and protect the card of FIG. 1 and its contents from contamination.

Indicated generally by numeral 44 in FIG. 3 is the sleeve member into which a wrapped card such as shown in FIGS. 1 and 2 may be inserted. The sleeve 44 comprises a pair of generally rectangular front and rear segments formed from a thin, flexible plastic film, 4-mil polyethylene being highly suitable. The length dimension of each of the two segments is slightly greater than the overall length dimension of the inner card member 10. Likewise, the width dimension of the film segments comprising the sleeve 44 is slightly greater than the width dimension of the card member 10. The two film segments are joined together along the edges 46 and 48 to form a sleeve or envelope which is open along the longitudinal side edges 50 and 52 thereof. Hence, the card member 10 with its complement of elastic band wound thereon may be inserted into the sleeve 44 through either side 50 or side 52.

When in place, the sleeve serves to protect the inner card, and more importantly, the band material wound thereon from contamination which may be caused by handling or the like. The surfaces of the rectangular segments forming the sleeve 44 provide a convenient location for the inclusion of printed information. Furthermore, the choice of polyethylene having a thickness of, for example, 0.004 inches is sufficiently transparent that it may be desirable to leave an area free from lettering or other graphic information so that the contents of the package can be viewed. This is especially advantageous when it is considered that the elastic bands used for vessel occlusion purposes are color coded and may be of differing lengths and/or widths. By gripping an end of a band accessible through either opening in the sleeve and pulling on that end, the band unwinds from the card without becoming tangled with that still remaining on the card and without the need for removing the inner card 10 from the sleeve 44.

Thus, it can be seen that there has been provided by this invention an arrangement whereby the various objects and advantages are achieved. Having now described the invention in specific detail and exemplified the manner in which it may be carried into practice, it will be readily apparent to those skilled in the art that various changes and modifications may be made to the basic arrangement involved without departing from its spirit or scope.

What is claimed is:

1. A dispenser package for elastic vessel occluding bands used in surgical procedures, comprising:
  (a) a generally rigid rectangular plastic card having first and second pairs of winding grooves formed inwardly into said card from opposed side edges thereof;
  (b) first and second slits formed respectively in the opposed end edges of said card;
  (c) a pair of tongue slits formed through said card proximate a medical transverse axes thereof and disposed inwardly of said opposed side edges forming first and second integrally formed tab elements, said tab elements being generally aligned and extending in opposite directions from one another;
  (d) at least two elastic strands, each having one end releasably held in one of said first and second slits formed in said end edges and the other end held by a respective one of said tab elements with the portion between said one and other ends of said strands being spirally wrapped about said card with only a single turn extending through each winding groove to thereby constrain the individual turns of said strands from lateral movement; and
  (e) a generally rectangular flexible plastic tubular sleeve member for receiving said plastic card therein.

* * * * *